United States Patent [19]

Thornfeldt

[11] Patent Number: 4,978,676

[45] Date of Patent: Dec. 18, 1990

[54] TREATMENT OF SKIN DISEASES WITH ARTEMISININ AND DERIVATIVES

[76] Inventor: Carl R. Thornfeldt, 1054 NW. 2nd Ave., Ontario, Oreg. 97914

[21] Appl. No.: 335,615

[22] Filed: Apr. 10, 1989

Related U.S. Application Data

[63] Continuation-in-part of Ser. No. 280,765, Dec. 6, 1988, abandoned, which is a continuation of Ser. No. 88,629, Aug. 24, 1987, abandoned.

[51] Int. Cl.$^5$ ............................................ A61K 31/335
[52] U.S. Cl. ...................................... 514/450; 514/863
[58] Field of Search ................................. 514/450, 863

[56] References Cited

PUBLICATIONS

Chemical Abstracts, 95:108182m (1981).

*Primary Examiner*—Leonard Schenkman
*Attorney, Agent, or Firm*—Townsend and Townsend

[57] ABSTRACT

Psoriasis, ultraviolet light induced skin conditions and tumors are successfully treated with topical or oral administration of artemisinin, dihydroartemisinin, its semisynthetic derivatives and its synthetic analogs. Viral tumors/diseases, hemorrhoids, and bullous skin diseases are also successfully treated with these topical compositions.

6 Claims, No Drawings

TREATMENT OF SKIN DISEASES WITH ARTEMISININ AND DERIVATIVES

CROSS REFERENCE TO RELATED APPLICATIONS

This application is a continuation-in-part of application Ser. No. 07/280,765, filed Dec. 6, 1988, which is a continuation of application Ser. No. 07/088,629, filed Aug. 24, 1987 both now abandoned.

BACKGROUND OF THE INVENTION

This invention relates to the topical and/or systemic treatment of psoriasis, ultraviolet radiation-induced skin diseases and skin tumors, and other related conditions with a class of compounds having sesquiterpene structures, including artemisinin, dihydroartemisinin, and derivatives and analogs of these compounds.

Psoriasis is a common skin disease characterized by hyperactive keratinocytes whose metabolism is increased nine-fold. The skin lesions generally are thick scales on sharply demarcated red plaques. The involved and uninvolved skin lesions have markedly elevated levels of the regulatory proteins putrescine and spermidine and suppressed local cell mediated immunity. No current therapies, including corticosteroids, retinoids, and immunosuppressive agents are effective in curing this disease, significantly decreasing the levels of these two polyamines, or stimulating lesional cell mediated immunity.

The polyamines of concern in this invention are generally low molecular weight, long chain, cationic aliphatic compounds with multiple amine and/or imino groups. These compounds are widely distributed in nature. Putrescine, spermidine, and spermine are the major polyamines found in man.

Ultraviolet radiation is invisible light that induces a number of diseases, including polymorphous light eruption, and collagen vascular diseases. Current therapies include topical sunscreens, immunosuppressive agents, corticosteroids, and surgery or destruction of the premalignant and malignant lesions.

Pemphigoid and pemphigus are autoimmune blistering diseases whose incidence increases with age and are life threatening. Unfortunately, a significant percentage of deaths are due to massive doses of the therapeutic agents, corticosteroids and immunosuppressives.

Artemisinin or Qinghaosu is a proven systemic antimalarial agent purified from the herb Artemisia Annua. Artemisinin is a sesquiterpene lactone with a peroxide grouping that is water insoluble but is extremely safe. There are single reports from China that artemisinin was (1) virustatic against influenza virus in chick embryo, (2) beneficial in a case of systemic lupus erythematosus, (3) suppresses humoral immunity, (4) stimulates cell mediated immunity, and (5) significantly decreases levels of all three human polyamines, especialy putrescine and spermidine.

In an effort to improve water solubility and decrease recurrences, scientists have developed semisynthetic derivatives and synthetic analogs of artemisinin. These compounds display the aforementioned sought after characteristics with the added benefit of increased antimalarial activity. These compounds have never been studied for therapeutic activity in any primary skin diseases or tumors and along with artemisinin have never been used as a topical treatment for any disease.

Treating primary skin disease and tumors with topically applied drugs improves safety, therapeutic success, and is much more cost effective. All topical drugs must penetrate the stratum corneum "barrier" to be effective. Nearly all drugs do not penetrate so penetration enhancers or vehicles have been developed to cross this barrier. When combined with the active drug, a dramatic improvement in therapeutic effectiveness occurs.

SUMMARY OF THE INVENTION

It has been discovered that compounds having structures which contain sesquiterpene groups are effective therapeutic agents useful in the treatment of a group of skin conditions. Included among these skin conditions are psoriasis; diseases and tumors induced by ultraviolet radiation or of viral origin, including blistering skin diseases; and hemorrhoids. Skin conditions induced by utraviolet radiation include polymorphous light eruption, collagen vascular disease, Bowen's disease, tumors and diseases of viral origin include warts, molluscum contagiosum, orf and ecthyma contagiosum.

The compounds which are discovered to have these properties, in accordance with this invention, include artemisinin; dihydroartemisinin; carbonate, sulfonate, ester, and ether derivatives of dihydroartemisinin, notably artemether, artesunate and artesunate salts, and dihydroartemisinin propyl carbonate; as well as the bisether artelinic acid. In the practice of the invention, formulations of these compounds are administered either parenterally, orally, or topically, For topical administration, the compounds are preferably formulated with vehicles which enhance the penetration of the formulations through the stratum corneum. These topical formulations are particularly effective in the treatment of viral tumors and diseases, blistering diseases and hemorrhoids.

In accordance with the invention, it has been discovered that compounds within this class significantly suppress all three polyamines major polyamines found in man, especially putrescine and spermine.

DETAILED DESCRIPTION OF THE INVENTION AND PREFERRED EMBODIMENTS

The compounds applied in accordance with the present invention are generally those whose molecular formulas include a sesquiterpene structure, preferably a sesquiterpene lactone with an attached peroxide. Within this group, those which are particularly preferred are artemisinin, dihydroartemisinin, semisynthetic derivatives of dihydroartemisinin including propyl carbonate dihydroartemisinin, artemether, artesunate, and other ethers, esters, carbonates and sulfonates, and the synthetic analog, artelinic acid. These compounds, when formulated for systemic administration or formulated with vehicles for topical application effectively treat psoriasis, collagen vascular diseases, polymorphous light eruption, xeroderma pigmentosa, and Bowen's diseases. These topical formulations also effectively treat hemorrhoids, viral induced diseases, pemphigoid and pemphigus. The collagen vascular diseases include lupus erythematosus, mixed connective tissue diseases, and dermatomyositis.

The compounds used in the present invention include those falling within the following generic formula:

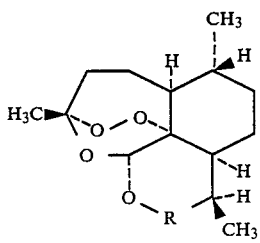 (I)

where R is either

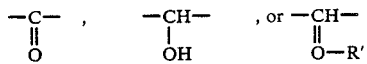

in which R' is as follows:

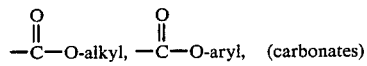

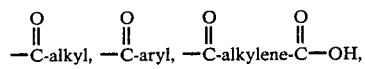

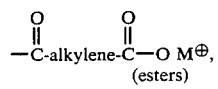

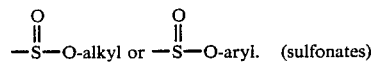

In the R' definition, the terms "alkyl" and "alkylene" preferably refer to lower alkyl or alkylene groups, notably $C_1$–$C_6$, with $C_1$–$C_4$ most preferred. Straight-chain and branched-chain groups are included, with straight-chain groups preferred. The term "aryl" preferably refers to phenyl and naphthyl, with phenyl the most preferred. The symbol M in Formula I is an alkali or alkaline earth metal, preferably sodium or potassium, with sodium the most preferably sodium or potassium, with sodium the most preferred. The ester in which R' is —C(O)—(CH$_2$)$_2$—CO$_2$H is known by the common names artesunic acid and artesunate, and the ester in which R' is —C(O)—(CH$_2$)$_2$—CO$_2$ Na$^\oplus$ is known as sodium artesunate.

Also included is the bis-ether, artelinic acid, having the formula:

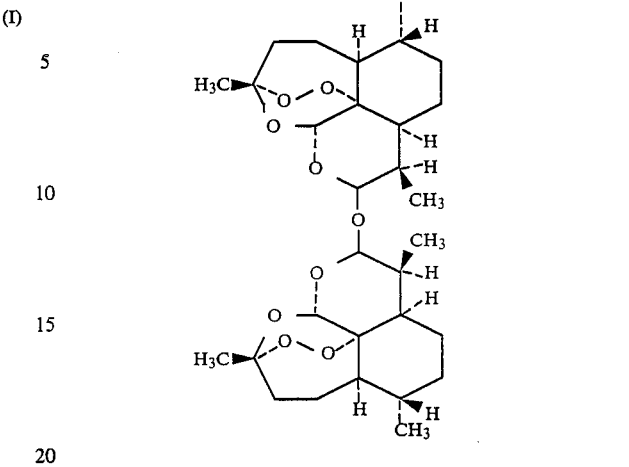

The concentrations of the sesquiterpene structure compounds in the formulations to be applied in the practice of the present invention are not critical and may vary widely. In most applications, however, best results will be obtained using formulations containing the compounds at levels of from about 0.01% to about 35% by weight, preferably from about 0.5% to about 15%. The amount of the compound actually administered for treatment will be a therapeutically effective amount, which term is used herein to denote the amount needed to produce a substantial clinical improvement. Optimal amounts will vary with the method of administration, and will generally be in accordance with the amounts of conventional medicaments administered in the same or a similar form. Topical application, for instance, is typically done from once to three times a day.

The topical formulations may further include one or more of the wide variety of agents known to be effective as skin penetration enhancers. Examples of these are 2-pyrrolidone, N-methyl-2-pyrrolidone, dimethylacetamide, dimethylformamide, propylene glycol, alcohol, dimethyl sulfoxide, and Azone. Additional agents may further be included to make the formulation cosmetically acceptable. Examples of these are fats, waxes, oils, dyes, fragrance, preservatives, stabilizers, and surface active agents. Keratolytic agents such as those known in the art may also be included. Examples are salicylic acid, sulfur, transretinoic acid and later generations of retinoids. The amounts of each of these various types of additive will be readily apparent to those skilled in the art, optimal amounts being the same as in other, known formulations designed for the same type of administration. Stratum corneum penetration enhancers, for example, will typically be included at levels within the range of about 0.1% to about 30% by weight, preferably from about 1% to about 15%.

The following example is offered for purposes of illustration, and is intended neither to define nor limit the invention in any manner.

EXAMPLE

Three patients with plaque psoriasis were treated with an ointment containing artemisinin at 1% by weight in a four-week, three-leg, open-paired comparison patch study. Trunkal or proximal extremity psoriatic plaques 1.5 to 3 centimeters in diameter that had been stable for at least four weeks were treated.

The test consisted of applying three different formulations to separate test areas on each of three patients. The formulations were as follows:

(a) 1% artemisinin ointment without added penetration enhancers;

(b) Aristocort A 0.1% cream, a Class IV corticosteroid; and (c) Diprolene ointment, a Class I corticosteroid.

Formulations (a) and (b) were applied twice daily and occluded with an elastic cloth bandage. The third was applied twice daily without occlusion. The lesions were examined weekly.

One patient experienced 100% clearing of all three test areas, while his untreated plaques improved by 50%, probably indicating some spontaneous remission. The three treated areas, however, cleared faster and more completely than the untreated areas, indicating that the formulations did have a therapeutic effect.

On the second patient, the plaque treated with formulation (a) improved by 75%. This plaque displayed 2+ erythema, but had no scale and was flat. By contrast, the plaque treated with formulation (b) improved by only 25%, while the plaque treated with formulation (c) remained unchanged.

On the third patient, the plaque treated with formulation (a) improved by 50% with 1+ violaceous erythema, but with a 1+ elevated and 1+ scaley peripheral rim. The plaque treated with formulation (b) improved by only 25%, while the plaque treated with formulation (c) was 100% clear except for 1+ post inflammatory hyperpigmentation.

The conclusion from these tests is that occluded artemisinin is superior to an occluded mid-potency topical corticosteroid, and comparable to a megapotent topical corticosteroid.

The foregoing is offered primarily for purposes of illustration. It will be readily apparent to those skilled in the art that further variations in the formulations and uses of the compounds beyond those described herein may be made without departing from the spirit or scope of the invention.

What is claimed is:

1. A method for the treatment of a subject suffering from psoriasis, said method comprising administering to said subject a therapeutically effective amount of a compound having the formula

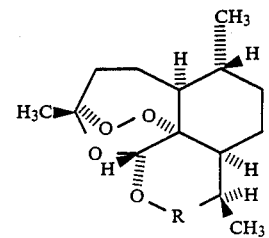

in which R is a member selected from the group consisting of

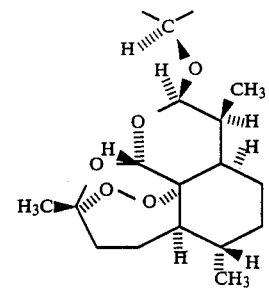

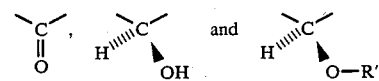

where R' is a member selected from the group consisting of

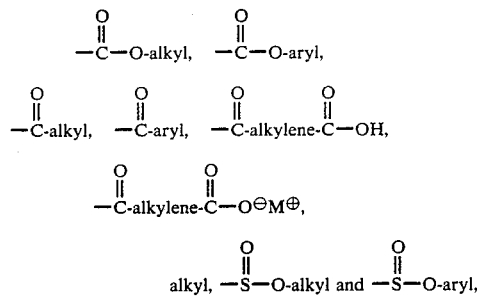

in which M is sodium or potassium.

2. A method in accordance with claim 1 in which said compound is a synthetic analog of dihydroartemisinin.

3. A method in accordance with claim 1 in which said compound is artelinic acid.

4. A method in accordance with claim 1 in which said compound is a semisynthetic derivative of dihydroartemisinin selected from the group consisting of esters, ethers, carbonates and sulfonates.

5. A method in accordance with claim 1 in which said compound is a member selected from the group consisting of artemisinin, dihydroartemisinin, artemether, artesunate, and dihydroartemisinin propyl carbonate.

6. A method in accordance with claim 1 in which said compound is a member selected from the group consisting of artemisinin, dihydroartemisinin, artemether, artesunate, and dihydroartemisinin propyl carbonate; and said method further comprises administering said compound in combination with a member selected from the group consisting of N-methyl-2-pyrrolidone and dimethylacetamide.

* * * * *